United States Patent [19]

VandenBerg

[11] Patent Number: Plant 7,512

[45] Date of Patent: Apr. 30, 1991

[54] CHRYSANTHEMUM PLANT NAMED DONNA

[75] Inventor: Cornelis P. VandenBerg, Salinas, Calif.

[73] Assignee: Yoder Brothers, Inc., Barberton, Ohio

[21] Appl. No.: 458,836

[22] Filed: Dec. 29, 1989

[51] Int. Cl.[5] ..... A01H 5/00
[52] U.S. Cl. ..... Plt./74
[58] Field of Search ..... Plt./74, 78

*Primary Examiner*—Howard J. Locker

*Attorney, Agent, or Firm*—Foley & Lardner, Schwartz, Jeffery Schwaab, Mack, Blumenthal & Evans

[57] ABSTRACT

A Chrysanthemum plant named Donna particularly characterized by its flat capitulum form; spooned daisy capitulum type; yellow ray floret color; diameter across face of capitulum of 63 to 75 mm when fully opened; medium plant height with spreading and prolific branching pattern; average natural season flowering date of August 28 in Salinas, Calif., and September 27 in Hightstown, N.J., uniform seven week photoperiodic flowering response to short days in photoperiodic controlled flowering programs; and durable, uniform performance.

3 Drawing Sheets

The present invention comprises a new and distinct cultivar of Chrysanthemum, botanically known as *Dendranthema grandiflora*, and referred to by the cultivar name Donna.

Donna, identified as 86-511001, was originated by the inventor Cornelis P. VandenBerg from a cross made in a controlled breeding program in Salinas, Calif., in 1986.

The female parent was the cultivar Goldmine, a yellow decorative disclosed in U.S. Plant Pat. No. 5,661. The male parent of Donna was an unnamed seedling identified as 80-N05008, a yellow single quilled duplex; that is, it has numerous tubular ray florets.

Donna was discovered and selected as one flowering plant within the progeny of the stated cross by Cornelis P. VandenBerg in September 1986, in a controlled environment in Salinas, Calif.

The first act of asexual reproduction of Donna was accomplished when vegetative cuttings were taken from the initial selection in November 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Donna are firmly fixed and are retained through successive generations of asexual reproduction.

Donna has not been observed under all possible environmental conditions. The phenotype may vary significantly with variations in environment such as temperature, light intensity and daylength.

The following observations, measurements and comparisons describe plants grown in controlled open areas in Salinas, Calif., and in Hightstown, N.J., and photoperiodic controlled programs conducted in Salinas, Calif. Rooted cuttings were established in soil and maintained outdoors under the natural temperature and daylength prevailing during June through October. Single pinching was practiced with all branches and buds retained.

The following traits have been repeatedly observed and are determined to be basic characterisitcs of Donna, which, in combination, distinguish this Chrysanthemum as a new and distinct cultivar:

1. flat capitulum form.
2. Spooned daisy capitulum type.
3. Yellow ray floret color.
4. Diameter across face of capitulum of from 63–75 mm when fully opened.
5. Medium plant height averaging 26 cm from soil line at time of flowering, based on June 15, planting under natural daylength in Hightstown, N.J.
6. Spreading and prolific branching pattern, with an average of eight (8) branches per plant after pinch two weeks after planting a rooted cutting in Hightstown, N.J.
7. Average natural season flowering date of August 28 in Salinas, Calif., and September 27 in Hightstown, N.J., based on several years of trial flowering.
8. Uniform seven week photoperiodic flowering response to short days in photoperiodic controlled flowering programs.
9. Durable, uniform performance.

The accompanying photographic drawings show typical influrescence and leaf characteristics of Donna, with the colors being as nearly true as possible with illustrations of this type.

Sheet 1 is a color photograph of Donna grown as pinched spray pot mum in a 15 cm pot.

Sheet 2 is a black and white photograph of three views of the inflorescence of Donna.

Sheet 3 is a black and white photograph showing the upper and under sides of the leaves of Donna at three stages of development (mature, intermediate and immature).

Of the commercial garden mum cultivars known to the inventor, the most similar in comparison to Donna is the cultivar Allure, a yellow daisy, disclosed in U.S. Plant Pat. No. 5,989. Reference is made to attached Chart A which compares certain characteristics of Donna to the same characteristics of Allure.

Similar traits are ray floret color and controlled response period. Donna has a spooned daisy capitulum type, while Allure has a daisy capitulum type. Donna also has a more spreading and prolific branching pattern, and a later natural season flowering date by three to five days than Allure.

In the following description color references are made to The Royal Horticultural Society Colour Chart. The color values were determined on plant material grown in a controlled greenhouse environment in Salinas, Calif., on Sept. 19, 1989.

Classification:

*Botanical.*—*Dendranthema grandiflora* cv Donna.

*Commercial.*—Spooned daisy spray pot mum and garden mum.

INFLORESCENCE

A. Capitulum:

*Form.*—Flat.

*Type.*—Spooned daisy.

*Diameter across face.*—63-75 mm when fully opened.

B. Corolla of Ray Florets:

*Color (general tonality from a distance of three meters).*—Yellow.

*Color (upper surface).*—(Spoon tips) 5A.

*Color (under surface).*—(Tubes) 5B to 5C.

*Shape.*—Straight, spoon tipped.

C. Corolla of Disc Florets:

*Color (mature).*—12A.

*Color (immature).*—Closest to 151C.

D. Reproductive Organs:

*Androecium.*—Present on disc florets only; scant pollen.

*Gynoecium.*—Present on both ray and disc florets.

PLANT

A. General Appearance:

*Height.*—Medium.

*Branching pattern.*—Spreading and prolific.

B. Foliage:

*Color (upper surface)*—147A.

*Color (under surface)*—147B.

*Shape.*—See photograph.

CHART A

COMPARISON OF DONNA AND ALLURE

| CHARACTERISTIC | DONNA | ALLURE |
|---|---|---|
| Ray Floret Color | Yellow | Yellow |
| Capitulum Form and Type | Flat spooned daisy | Flat daisy |
| Branching Pattern | Spreading and prolific | Semi-spreading |
| Controlled Response | 7 weeks | 7 weeks |
| Average Natural Season Flower date: | | |
| In Salinas, California: | August 28 | August 25 |
| In Hightstown, New Jersey: | September 27 | September 22 |

Comparisons Made of Plants Grown Under Natural Season Outdoor Conditions In Salinas, California and in Hightstown, New Jersey

I claim:

1. A new and distinct Chrysanthemum plant named Donna, as described and illustrated.

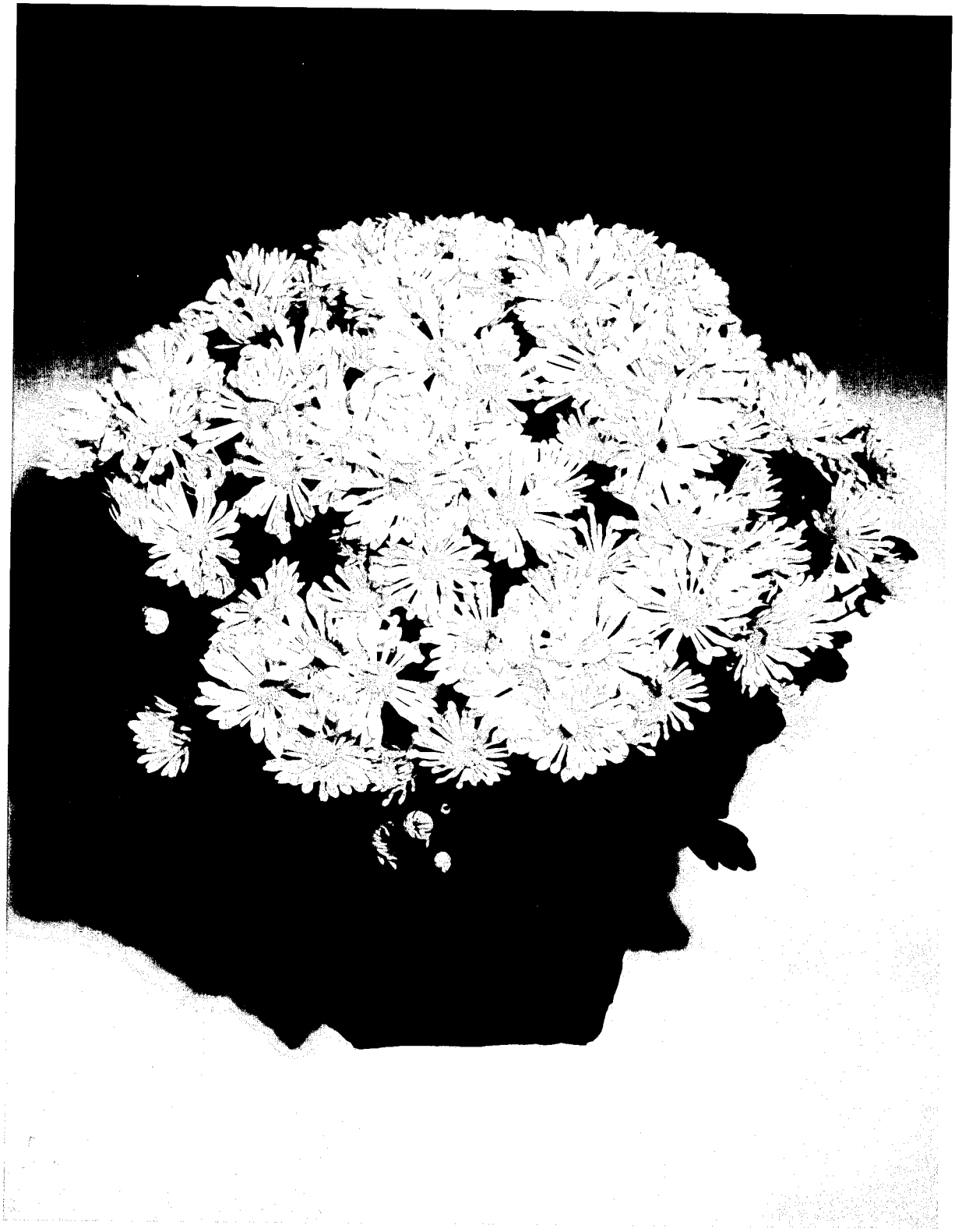

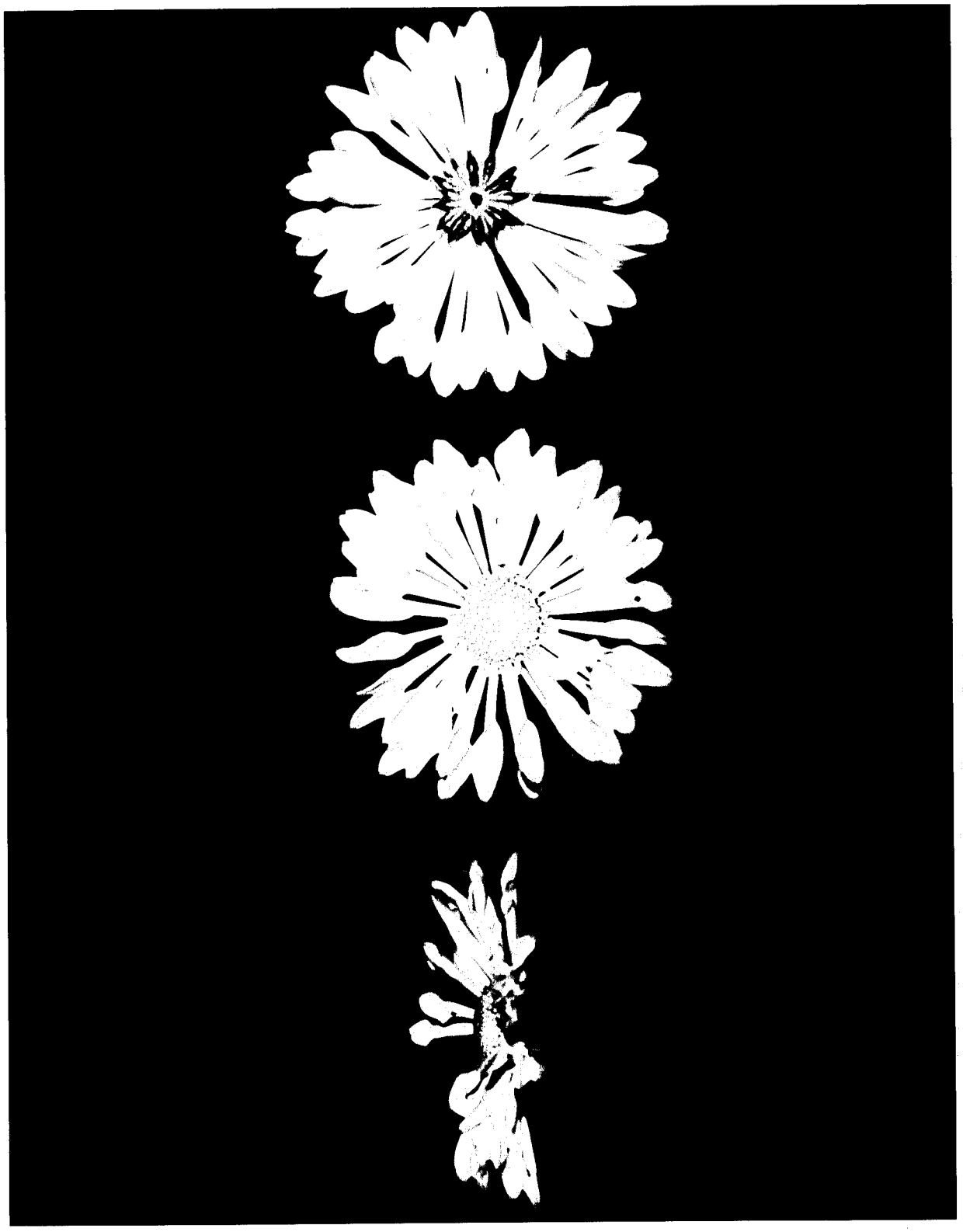

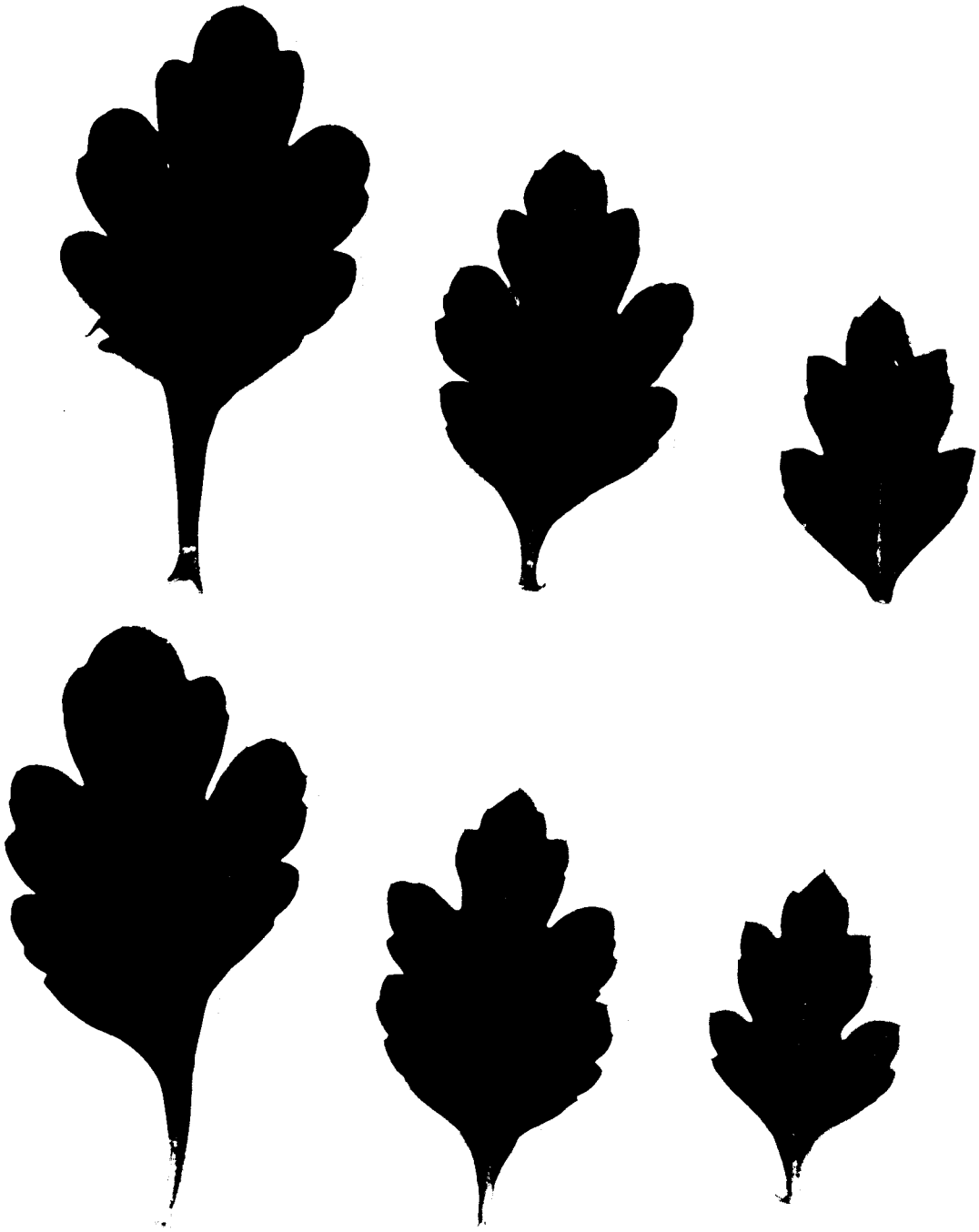

* * * * *